US011590028B2

(12) United States Patent
Hayes et al.

(10) Patent No.: US 11,590,028 B2
(45) Date of Patent: Feb. 28, 2023

(54) SELECTIVELY ATTACHABLE VISORS FOR FIELD MASKS

(71) Applicant: Z2D, LLC, Portland, OR (US)

(72) Inventors: Joseph Hayes, Portland, OR (US); Leslie Hayes, Portland, OR (US)

(73) Assignee: Z2D LLC, Portland, OR (US)

( * ) Notice: Subject to any disclaimer, the term of this patent is extended or adjusted under 35 U.S.C. 154(b) by 218 days.

(21) Appl. No.: 17/017,975

(22) Filed: Sep. 11, 2020

(65) Prior Publication Data
US 2021/0069020 A1    Mar. 11, 2021

Related U.S. Application Data (60) Provisional application No. 62/898,667, filed on Sep. 11, 2019.

(51) Int. Cl.
*A61F 9/04* (2006.01)
*A63B 71/10* (2006.01)

(52) U.S. Cl.
CPC .............. *A61F 9/045* (2013.01); *A63B 71/10* (2013.01)

(58) Field of Classification Search
CPC ....... A61F 9/045; A63B 71/10; A42B 1/0184; A42B 1/0182; A42B 3/22; A42B 3/227; A42B 3/20
See application file for complete search history.

(56) References Cited

U.S. PATENT DOCUMENTS

| | | | | |
|---|---|---|---|---|
| 3,239,842 A | * | 3/1966 | Marchello | A42B 3/227 2/10 |
| 3,400,407 A | | 9/1968 | Aileo | |
| 3,927,421 A | * | 12/1975 | Simon | A42B 3/0493 2/12 |
| 4,333,180 A | | 6/1982 | Bay | |
| 4,575,875 A | * | 3/1986 | Dawson | A42B 3/227 2/10 |
| 4,700,411 A | * | 10/1987 | Kawasaki | A42B 3/227 2/425 |
| 4,736,466 A | * | 4/1988 | Kallstrom | A63B 71/10 2/427 |
| 5,070,545 A | * | 12/1991 | Tapia | A42B 1/248 2/171.1 |
| 5,177,810 A | * | 1/1993 | Minton | A42B 1/0184 2/10 |
| 5,333,328 A | * | 8/1994 | Roberts | A42B 3/227 2/12 |
| 5,335,371 A | * | 8/1994 | Spessard | A63B 71/10 2/9 |
| 5,437,062 A | | 8/1995 | Douglas | |
| 5,571,220 A | | 11/1996 | Hall | |

(Continued)

*Primary Examiner* — F Griffin Hall
(74) *Attorney, Agent, or Firm* — Chernoff, Vilhauer, McClung & Stenzel LLP (57) ABSTRACT

A visor that can be removably attached to a variety of field masks, including those used in softball and baseball and other sports, to protect the user from weather elements and minimize sun damage while not affecting play and withstanding movement. In some embodiments, the visor may include a curvilinear base having at least one recess. The visor may additionally include a brim attached to, or formed with, the base. The visor may further include a fastener received in the at least one recess, where the fastener is configured to secure the visor to the field mask.

14 Claims, 5 Drawing Sheets

(56) References Cited

U.S. PATENT DOCUMENTS

| | | | | |
|---|---|---|---|---|
| 5,621,923 A * | 4/1997 | Tapocik | ............ | A42B 3/227 2/12 |
| 5,675,843 A * | 10/1997 | Grim | ............ | A42B 3/227 2/12 |
| 5,699,556 A * | 12/1997 | Chen | ............ | A61F 9/029 2/9 |
| 5,829,065 A * | 11/1998 | Cahill | ............ | A42B 3/324 2/418 |
| 5,896,587 A * | 4/1999 | Gentry | ............ | A42B 3/08 2/12 |
| 6,009,555 A * | 1/2000 | Siprut | ............ | A42B 3/227 2/209.3 |
| 6,009,561 A * | 1/2000 | Bullock | ............ | A42B 3/227 24/297 |
| 6,170,084 B1 * | 1/2001 | Gordon | ............ | A42B 3/28 2/12 |
| 6,687,909 B1 * | 2/2004 | Witkoff | ............ | A42B 3/28 2/424 |
| 6,718,559 B1 * | 4/2004 | Davidson | ............ | G09F 21/02 24/324 |
| 7,430,763 B1 * | 10/2008 | Santos | ............ | A42B 3/20 2/9 |
| D607,608 S * | 1/2010 | Taylor | ............ | D29/109 |
| 9,433,253 B2 * | 9/2016 | McKinney | ............ | A42B 3/227 |
| 9,491,980 B2 * | 11/2016 | Wako | ............ | A42B 3/223 |
| 10,070,677 B2 * | 9/2018 | Durham | ............ | A42B 3/0406 |
| 10,564,444 B2 * | 2/2020 | Clark | ............ | G02C 3/02 |
| 10,743,603 B2 * | 8/2020 | McDavitt | ............ | A42B 3/28 |
| D922,690 S * | 6/2021 | Fukuyama | ............ | D29/122 |
| 2006/0090235 A1 * | 5/2006 | Clark | ............ | B65D 81/363 2/12 |
| 2007/0011794 A1 * | 1/2007 | Wang Lee | ............ | A42B 3/227 2/10 |
| 2012/0284905 A1 * | 11/2012 | Kim | ............ | A42B 3/226 2/424 |
| 2015/0173444 A1 * | 6/2015 | O'Dell | ............ | A42B 3/042 2/422 |
| 2017/0027265 A1 | 2/2017 | Bryan et al. | | |
| 2017/0367425 A1 * | 12/2017 | Chen | ............ | A42B 3/046 |
| 2018/0295925 A1 | 10/2018 | Gagliardo et al. | | |

* cited by examiner

SELECTIVELY ATTACHABLE VISORS FOR FIELD MASKS

CROSS-REFERENCE TO RELATED APPLICATIONS

This application claims the benefit of U.S. Provisional Patent Application Ser. No. 62/898,667 filed on Sep. 11, 2019 and entitled VISORS. The complete disclosure of the above application is hereby incorporated by reference for all purposes.

BACKGROUND OF THE INVENTION

The present invention is directed to protective sport headgear, and more specifically to a visor that removably attaches to field masks used to play sports.

Softball and baseball are popular sports in the United States, with a combined total of five million teenage players annually and growing. In 2013, around a quarter of all softball injuries were to the head, face or neck. These injuries may range anywhere from broken noses, knocked-out teeth, lacerations, to concussions. Due to the close proximity and speed at which the pitchers throw the ball, batters generally use protective face masks and other gear to minimize the risk of injury. In recent years, defensive players in the field have also begun to wear protective face masks.

A softball or baseball field mask generally includes three connected structures assembled to fit over a player's head. First, the centerpiece generally includes a cross bar assembly that covers a player's facial area from the eyes and below, and oftentimes the centerpiece also includes a chin cup or pad for added security and comfort. Common materials for the centerpiece are steel, titanium, or other types of light weight metal. Second, an upper piece frames the player's eye and forehead area from the temples, over the ears, and across the forehead. The upper piece typically has padding inserted for added stability, fit and comfort. The upper piece is generally firmly affixed to the centerpiece and the two pieces form the bulk of the field mask and provide protection for the head. The final structure generally comprises adjustable straps that connect to the upper piece from the top and the sides, where the straps go over a player's head from the top to the back and secure the field mask position on the player's head. The straps may be made from durable fabric, nylon and other materials.

While these field masks greatly help prevent injuries, when the field mask is worn, the upper piece and the straps typically preclude the wearer from wearing a traditional visor or ball cap. This means the wearer must contend with the glare and U.V. damage from the sun and waterdrops from the rain, as well as any other weather elements, which can negatively affect visibility. Prolonged exposure to the sun may also cause permanent damage to a player's skin. If the player wears glasses, rain can greatly obscure visibility if there is nothing to shield it, and the player may have to wipe the glasses to resume playing.

What is desired, therefore, is an assembly that includes a field mask visor that can be removably attached to field masks, to protect the user from weather elements and minimize sun damage while not affecting play and withstanding movement.

BRIEF DESCRIPTION OF THE SEVERAL DRAWINGS

For a better understanding of the invention, and to show how the same may be carried into effect, reference will now be made, by way of example to the accompanying drawings, which.

DETAILED DESCRIPTION OF PREFERRED EMBODIMENTS

Figure 1:
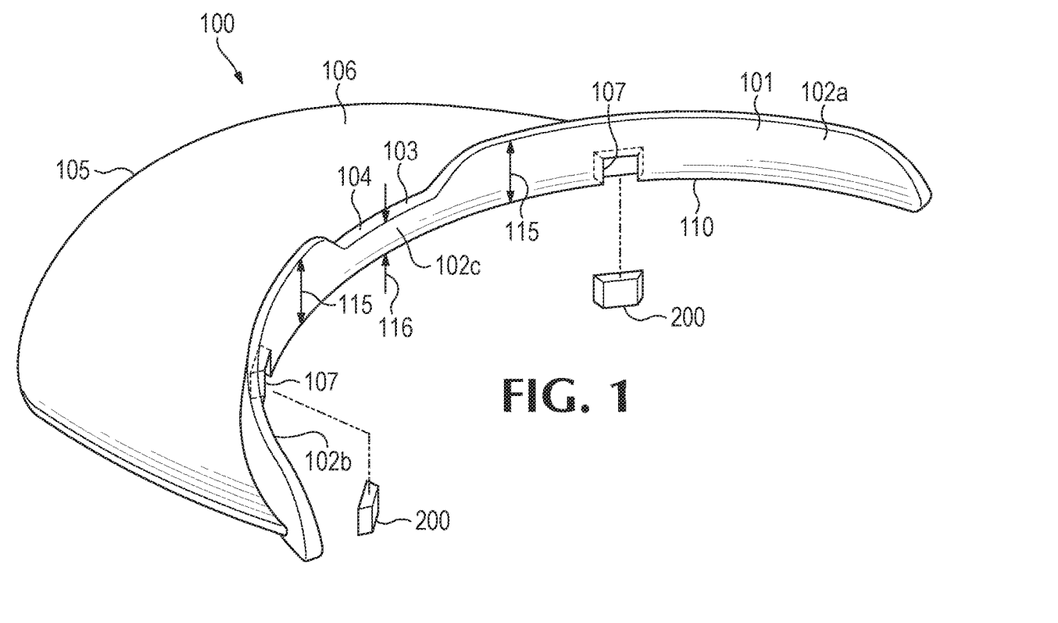
FIGS. 1-3 are various perspective views of an illustrative example of a visor of the present disclosure.
Figure 2:
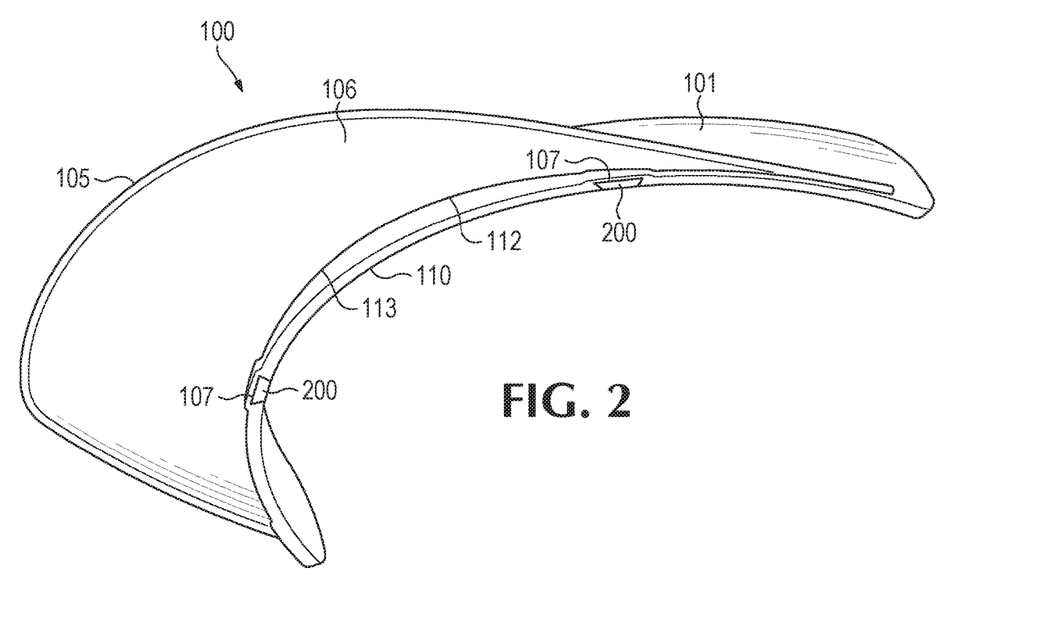
Figure 3:
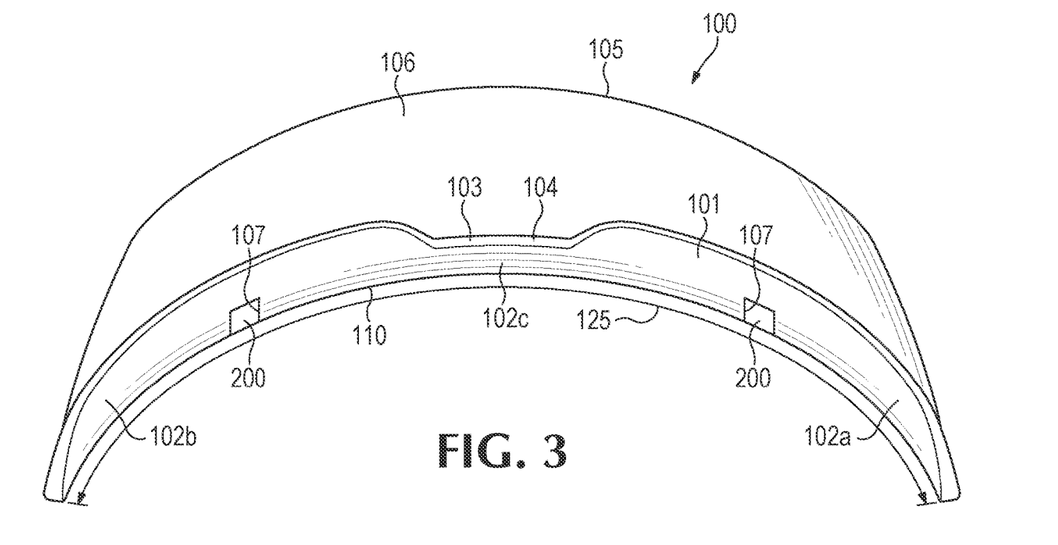

Referring to FIGS. 1-4, an illustrative example of a removable or selectively attachable or detachable visor 100 is shown, which is used to shield a user's eyes from the sun, rain and other weather elements. In some embodiments, the visor 100 includes a generally circular base 101 and a brim band or brim 106. The curvature of the circular base 101 of the visor 100 may correspond to and follow the curvature of the upper piece of a field mask (such as field mask 300 in FIG. 5) to ensure a proper fit. In some embodiments, the base may have a curvilinear shape with a length 125 that allows the base to partially wrap around or encircle the upper piece of a field mask to at least partially cover the forehead and temple areas of the field mask. As shown in FIGS. 1-3, the base 101 may be comprised of two side portions 102a, 102b, and a center or central portion 102c. In some embodiments, each of the first and second side portions may have a first height 115 measured perpendicular to the length 125 of the base, the central portion having a second height 116 measured perpendicular to the length, the second height 116 may be less than the first height 115 to define a gap 103 between the first and second side portions. In the embodiment shown in FIGS. 1-3, the center portion 102c of the circular base 101 may have at least one opening or gap 103 to accommodate or receive one or more portions of the straps of the field mask (such as straps 303 in FIG. 5) so that those straps do not interfere with attachment of the visor 100 to the field mask. The openings or gap 103 may have curved or rounded edges 104, and the width of the openings may vary depending on the strap width passing through. In some embodiments, there may not be a gap on the visor.

Referring to FIGS. 2-3, the brim 106 may be attached to, or formed with, the attachment region 112 of the circular base 101. A portion 110 of the circular base 101 may be below the brim 106. The brim may be generally perpendicular to the base, so as to prevent obstructing a user's vision while also serving as a shield to weather elements. In some embodiments, the brim 106 may include a starting rim 113, a terminal edge 105 that may be rounded, and the brim 106 may be large enough to sufficiently cover and/or shield a user's eyes from weather elements. The brim may be composed of any material that is light-weight, weather-proof and durable, and in some instances may be see-through or translucent to allow a user full range of vision. The brim may also come in different colors, either for aesthetic or functional purposes.

As shown in FIGS. 1-4, in some embodiments, the visor 100 may be fastened to the upper component piece 301 of the field mask 300 (shown in FIG. 5) through fasteners such as magnets 200, where the magnets 200 are inserted or received into the circular base 101 of the visor. When engaged, the magnets 200 may allow the visor 100 to firmly fasten onto a portion of the field mask while also being adjustable. The circular base 101 may have multiple receiving recesses or cutouts 107 to receive the magnets 200.

In some embodiments, the cutouts 107 may be positioned such that the magnets 200 are not visible when the visor 100 is attached to a field mask. The magnets may also be covered or encompassed by the base. In other embodiments, materials such as Velcro, buttons, adhesive tape and others may be used in the cutouts to fasten the visor to the field mask. The cutouts may be placed generally along the length of the curvilinear base 101, and in some instances may be placed around both sides of the temple area of the upper piece of the field mask, so as to add to the stability of the fasteners when the visor is in use. The cutouts 107 may be any suitable shape(s). Additionally, the circular base 101 may include any suitable number of the cutouts 107.

Figure 4:
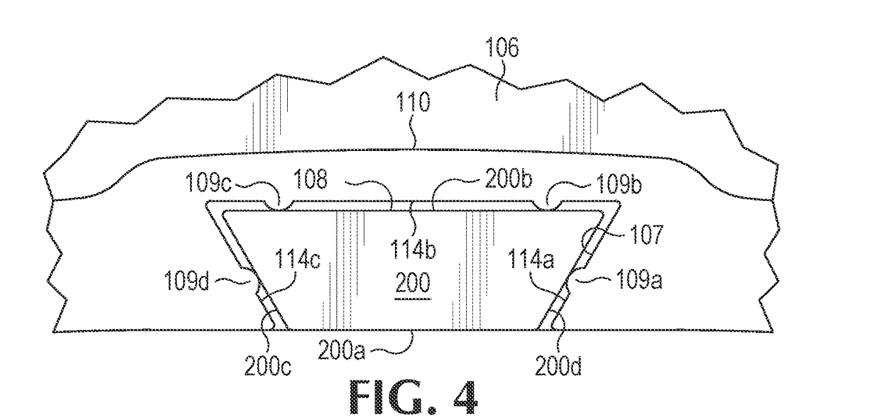
FIG. 4 is a partial view of the visor of FIGS. 1-3 showing an example of a recess receiving a fastener.

Referring to FIGS. 3-4, in some embodiments, the shape of the cutouts or apertures 107, as well as the corresponding fasteners, such as the magnets 200, may be in a generally trapezoidal shape, where the shorter side of the two parallel sides of the trapezoid carveout 107 is positioned closer to the side facing the field mask 300, and the longer side 108 is positioned more inwards toward the visor rim or terminal edge 105, away from the field mask 300. Magnets 200 include opposed parallel sides 200a and 200b and opposed nonparallel or inclined sides 200c and 200d. Parallel sides 200a and 200b may also be referred to as "bases" with 200a being the "short base" and 200b being the "long base." Additionally, nonparallel sides 200c and 200d may also be referred to as "legs."

The trapezoidal shape of the cutouts 107 and corresponding magnets 200 allow for the magnets 200 to fit into the receiving cutouts 107 more tightly, and having the narrow sides of the magnets 200 facing outwards toward the circular base 101 prevents the magnets from falling out when the visor 100 is in use. In other words, cutouts 107 is shaped to receive magnets 200 such that, when magnets 200 are received in cutouts 107, long base 200b of the magnets 200 is adjacent the brim 106 and short base 200a of the magnets 200 is spaced from the brim 106 relative to the long base 200b. Further, placing the shorter base of the trapezoid fastener adjacent to the field mask upper piece and spacing the longer base away from the field mask prevents the fastener from being removed along with the visor, when a user is removing the visor from the field mask after a game, or when weather conditions change during a game. In other embodiments, the cutouts 107 or the magnets 200 (or other fasteners) may not be trapezoidal and may be in other shapes, such as triangular or circular, so long as the same considerations apply to prevent the magnets and/or other fasteners from easily falling out. In some embodiments, the magnets or other fasteners may be embedded in the base.

In some embodiments as shown in FIG. 4, the cutout 107 may include or be defined by internal walls 114a, 114b, 114c, and ribs 109 positioned on the surface of one or more of the internal walls, such as ribs 109a-109d. The ribs 109 may be configured to minimize the space and any gaps between the corresponding magnet 200 and the cutout 107. The ribs 109 allow the cutouts to grip the magnets 200 and minimize inconsistencies in the cutout and magnet during production and manufacture. In other words, the ribs 109 secures the magnets 200 to the cutouts. Due to production error, there may be times where the cutout is not a perfect fit to the magnet or fastener. The ribs thus allow for minor adjustment and prevent waste of materials during manufacture. The ribs 109 may have any suitable shape(s) and may be positioned in any suitable portions of the cutout 107. Additionally, each cutout 107 may include any suitable number of the ribs 109.

Figure 5:
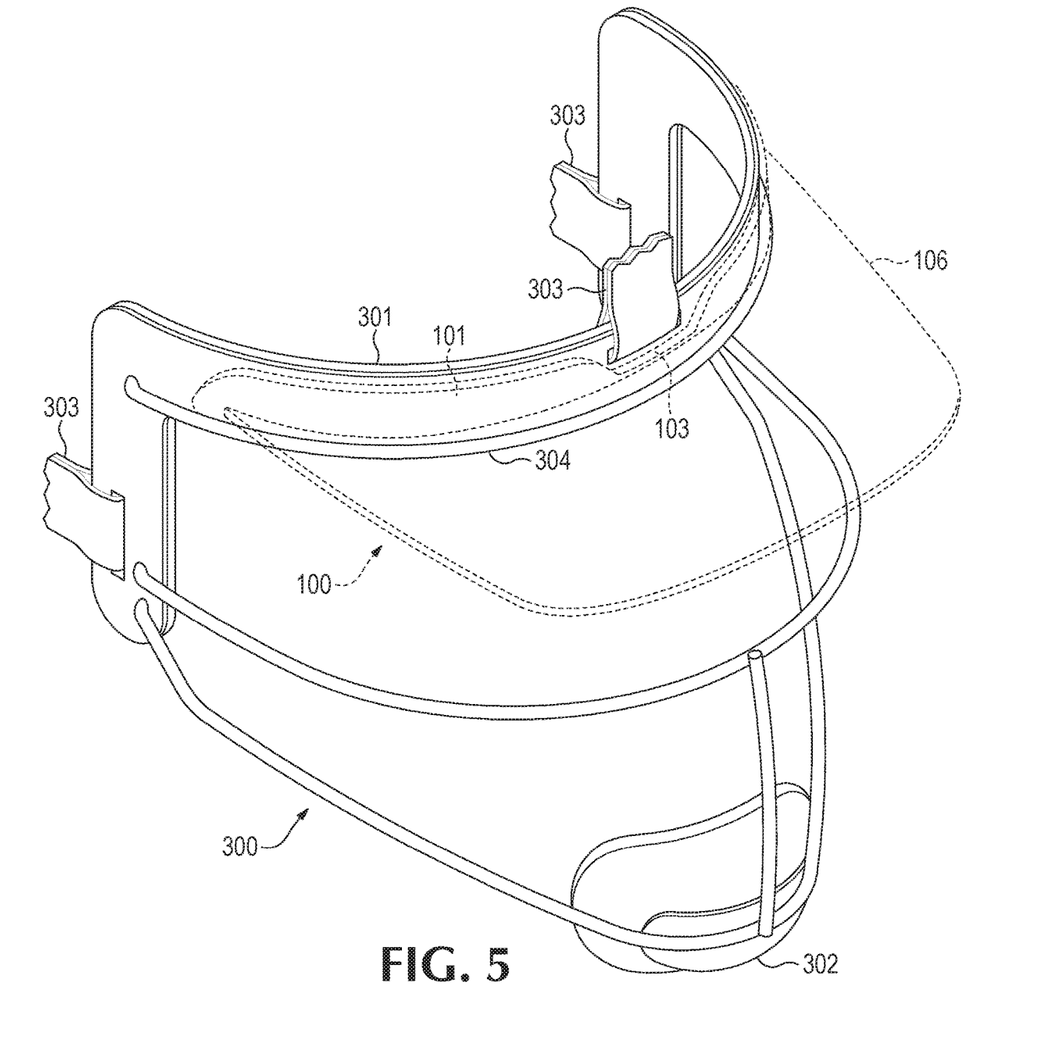
FIG. 5 is a perspective view of the visor of FIGS. 1-3 attached to an example of a field mask.

Referring to FIG. 5, an example of a visor 100 placed on a field mask 300 is shown. The visor 100 may be removably fastened onto the field mask 300, where the visor 100 is positioned directly adjacent to the upper piece 301 of the field mask 300, above the centerpiece 302 that includes a cross bar assembly. As shown in FIG. 5, the upper piece 301 of the field mask 300 may include protruding rims 304 on the bottom edge of the upper piece. In a preferred embodiment, a portion of the visor 100 may be positioned directly onto the rims 304 when fastened, so that the rims and visor are in direct contact, further adding to the stability and support of the visor. In some embodiments, as shown in FIG. 3, the placement of the magnets 200 may also determine which portions of the visor 100 contact and fasten to the upper piece 301 of the field mask 300. As shown in FIG. 5, the center portion 102c of the circular base 101 of the visor 100 may have openings 103 to make room for the straps 303 of the field mask 300 and accompanying strap clips and adjusters, or any additional components of the field mask.

Figure 6:
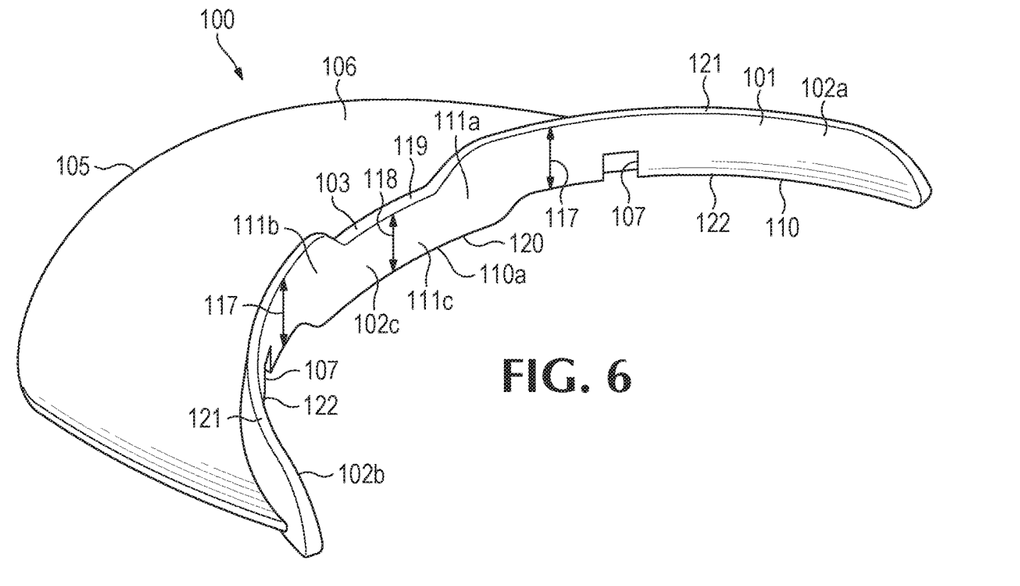
FIGS. 6-7 are various perspective views of an additional example of a visor of the present disclosure.
Figure 7:
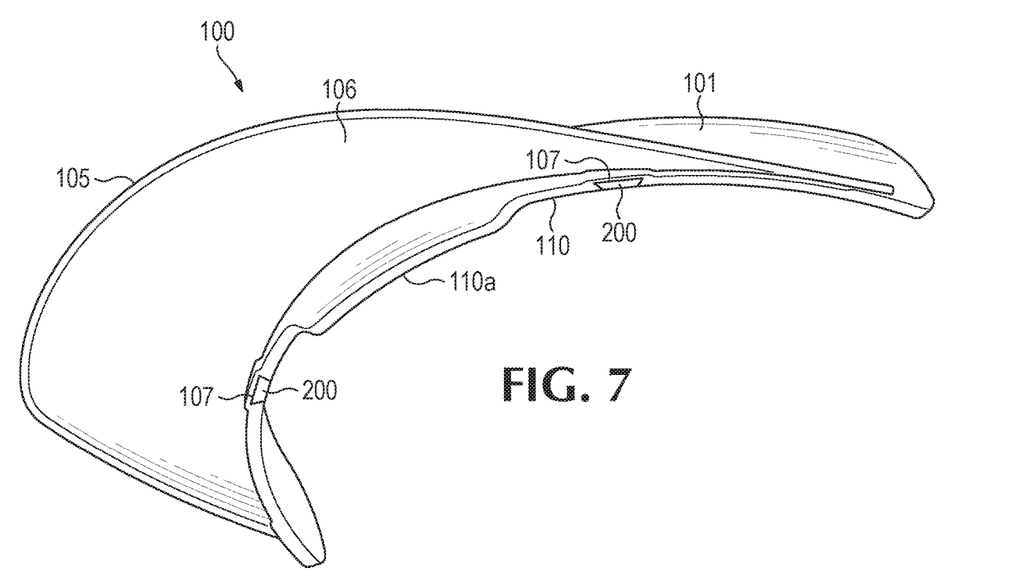
Figure 8:
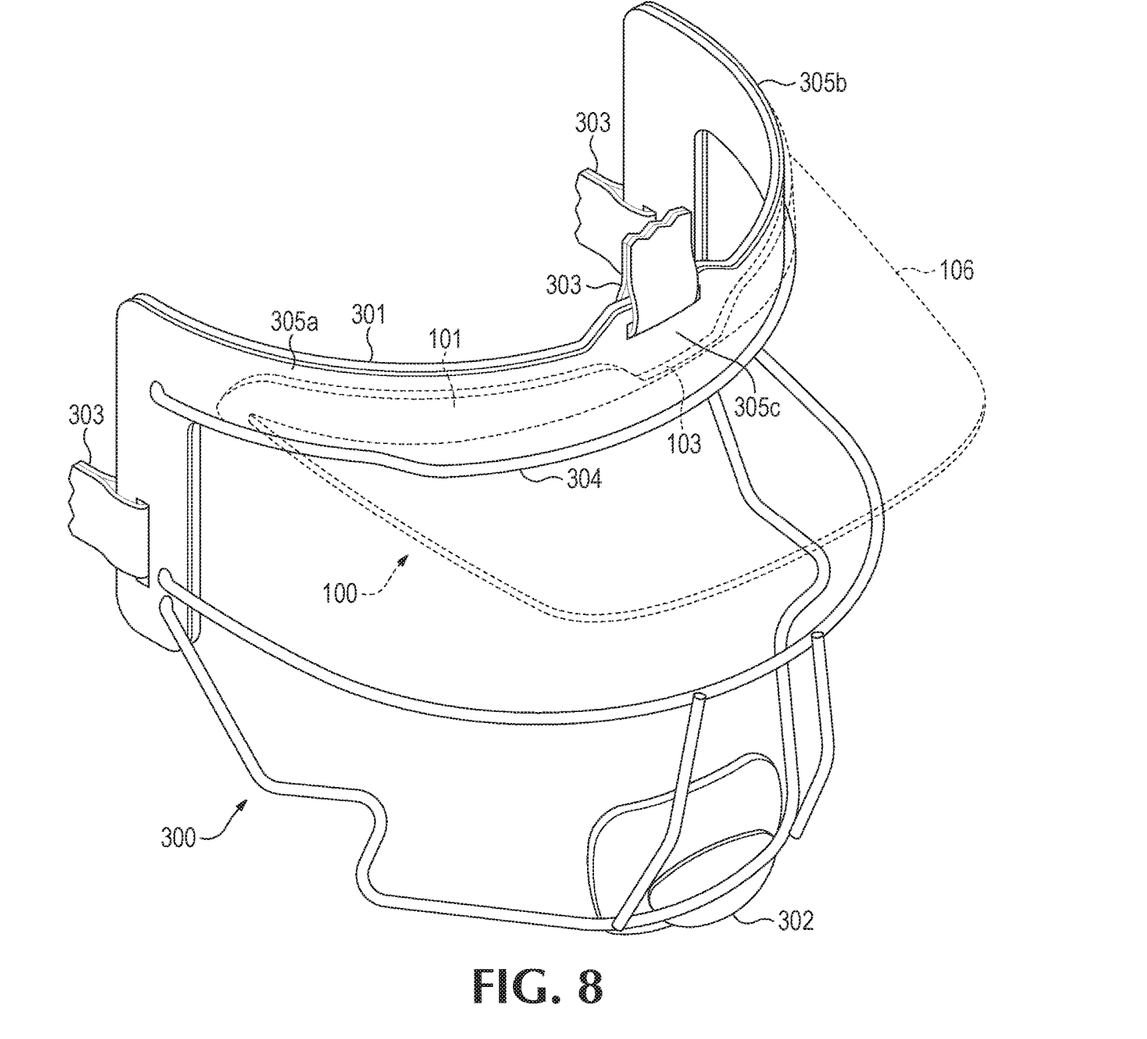
FIG. 8 is a perspective view of the visor of FIGS. 6-7 attached to another example of a field mask.

Referring to FIGS. 6-8, an additional example of visor 100 is shown having a portion 110 of the circular base 101 extend below the brim 106, the extended portion having an additional protruding area 110A that allows the visor 100 to accommodate the field mask 300 as shown in FIG. 8, so that portions of the visor 100 may be positioned directly onto the rims 304 on the edge of the field mask 300. Referring to FIG. 8, the field mask 300 is shown where the upper piece has a first side part 305a, a second side part 305b, and a center part 305c, where the center part of the upper piece has an increased height, i.e., the rims 304 dip or curve downwards toward the centerpiece of the mask.

As shown in FIG. 6, in order to accommodate and fit better with the mask 300, the visor base may have a first 102a and second side portion 102b, where the portions have a top margin 121 and a bottom margin 122, as well as a center portion 102c. The center portion 102c of the visor base 101 may also have top margin 119 and a bottom margin 120, a corresponding first 111a and second part 111b, as well as a center part 111c. The first and second parts 111a and 111b may have a height 117 perpendicular to the length of the brim 106, and the central part 111c may have a height 118. In some embodiments, the height 118 of the central part 111c of the center portion 102c may be less than the height 117 of the first and second parts 111a-b. The increased height of the center part allows the visor to contact the rims 304 of the center part 111c of the upper piece, further increasing stability of the visor and mask. In some embodiments, the bottom margin 120 of the central portion 102c may extend past the bottom margin 122 of the first and second side portions, so as to form a protruding area 110A.

Although the visors of the present disclosure are described to be selectively attachable and detachable to field masks, the visors may additionally, or alternatively, be selectively attachable and detachable to other facial and/or head ware, including other types of masks. In the instance where the fasteners are magnets, the visor may be selectively attached to any headwear made from metal, so long as the curvature of the visor base is generally aligned with the frontal part of the of the headwear.

EXAMPLE FEATURES

This section describes additional aspects and features of visors and/or field masks, presented without limitation as a series of paragraphs, some or all of which may be alphanumerically designated for clarity and efficiency. Each of these paragraphs can be combined with one or more other paragraphs, and/or with disclosure from elsewhere in this application in any suitable manner. Some of the paragraphs below expressly refer to and further limit other paragraphs, providing, without limitation, examples of some of the suitable combinations.

A1. A visor selectively attachable to a field mask, comprising:
 a generally circular base having at least one recess;
 a brim attached to, or formed with, the generally circular base; and
 a fastener received in the at least one recess, the fastener configured to secure the visor to the field mask.

A2. The assembly of paragraph A1, wherein the fastener is a magnet.

A3. The assembly of paragraph A2, wherein the magnet has a trapezoidal shape.

A4. The assembly of any of paragraphs A2-A3, wherein the at least one recess has a trapezoidal shape that corresponds to the trapezoidal shape of the magnet.

B1. A visor selectively attachable to a field mask, comprising:
 a generally circular base having top and bottom protruding edges configured to attach to top and bottom edges of a portion of the field mask, respectively; and
 a brim attached to, or formed with, the generally circular base.

C1. A detachable visor in combination with a field mask, wherein the field mask includes a frame, a centerpiece attached to the frame, the centerpiece having a cross bar assembly for covering a player's facial area, and one or more adjustable straps configured to secure the frame to the player; and wherein the visor includes:
 a generally circular base having at least one recess;
 a brim attached to, or formed with, the generally circular base; and
 a fastener received in the at least one recess, the fastener configured to secure the visor to the frame of the field mask.

D1. A detachable visor in combination with a field mask, wherein the field mask includes a frame, a centerpiece attached to the frame, the centerpiece having a cross bar assembly for covering a player's facial area, and one or more adjustable straps configured to secure the frame to the player; and wherein the visor includes:
 a generally circular base having top and bottom protruding edges configured to attach to top and bottom edges of the frame of the field mask, respectively; and
 a brim attached to, or formed with, the generally circular base.

It will be appreciated that the invention is not restricted to the particular embodiment that has been described, and that variations may be made therein without departing from the scope of the invention as defined in the appending claims, as interpreted in accordance with principles of prevailing law, including the doctrine of equivalents or any other principle that enlarges the enforceable scope of a claim beyond its literal scope. Unless the context indicates otherwise, a reference in a claim to the number of instances of an element, be it a reference to one instance or more than one instance, requires at least the stated number of instances of the element but is not intended to exclude from the scope of the claim a structure or method having more instances of that element than stated. The word "comprise" or a derivative thereof, when used in a claim, is used in a nonexclusive sense that is not intended to exclude the presence of other elements or steps in a claimed structure or method.

We claim:

1. A selectively attachable visor for a field mask, comprising:
 an elongate base having a curvilinear shape across its length to partially wrap around an upper piece of the field mask, the elongate base having a first side portion, a second side portion, and a central portion disposed between the first and second side portions, a substantial portion of each of the first and second side portions having a first height measured perpendicular to the length, the central portion having a second height measured perpendicular to the length, the second height being less than the first height to define a gap between the first and second side portions, the gap being sized to receive a portion of at least one strap of the field mask when the base is partially wrapped around the upper piece of the field mask, the base including at least one recess;
 a brim band having a starting rim and a terminal edge, the brim band is generally perpendicular to the base, and the starting rim is attached to, or formed with, the base; and
 at least one fastener received in the at least one recess, the at least one fastener secures the base to the field mask when the base is partially wrapped around the upper piece of the field mask.

2. The selectively attachable visor of claim 1, wherein the central portion has the second height throughout its length.

3. The selectively attachable visor of claim 1, wherein the central portion includes first and second end parts and a central part disposed between the first and second end parts, the first and second end parts having a third height that is greater than the first height, and the central part having the second height.

4. The selectively attachable visor of claim 3, wherein the starting rim is attached to, or formed with, an attachment region of the base, the attachment region spanning the first side portion, the first end part, the central part, the second end part, and the second side portion.

5. The selectively attachable visor of claim 4, wherein the attachment region is positioned on the central part such that the attachment region is disposed between the gap and a substantial portion of the central part, the substantial portion of the central part contacting the upper piece of the field mask when the base is partially wrapped around the upper piece of the field mask.

6. The selectively attachable visor of claim 1, wherein the at least one fastener is a magnet.

7. The selectively attachable visor of claim 6, wherein the at least one recess has a trapezoidal shape and the magnet has a corresponding trapezoidal shape having a long base, a short base parallel and opposed to the long base, and opposed legs to fit in the at least one recess.

8. The selectively attachable visor of claim 7, wherein the at least one recess is shaped such that the long base of the magnet is adjacent to the brim band and the short base of the magnet is spaced from the brim band relative to the long base.

9. The visor of claim 1, wherein the at least one recess is defined by a plurality of internal walls, wherein one or more surfaces of the internal walls include ribs.

10. The visor of claim 9, wherein the ribs are evenly spaced.

11. A selectively attachable visor for a field mask, comprising:

a curvilinear base having a length to partially encircle an upper piece of the field mask, wherein the base further includes:
  a first side portion, a second side portion, and a central portion disposed between the first and second side portions, each of the first and second side portions having a first height measured perpendicular to the length, the central portion having a second height measured perpendicular to the length from a top margin and a bottom margin, where the second height is less than the first height to define a gap between the first and second side portions in order to accommodate a portion of at least one strap of the field mask,
  at least one trapezoidal aperture placed along its length, the at least one trapezoidal aperture defined by a plurality of internal walls, the at least one trapezoidal aperture is positioned along the length that generally corresponds to a temple area of the upper piece of the field mask, and
  a magnet received in the at least one trapezoidal aperture to secure the base to the field mask, wherein the magnet is shaped to correspond with the at least one trapezoidal aperture, wherein at least one internal wall of the plurality of internal walls includes ribs to secure the magnet to the at least one trapezoidal aperture; and
a brim attached to, or formed with, the base, the brim being generally perpendicular to the base and positioned such that the brim is spaced between the top and the bottom margin of the base.

12. The visor of claim 11, wherein the central portion includes first and second end parts and a middle part disposed between, the first and second end parts having a third height that is greater than the first height, and the middle part having the second height.

13. A selectively attachable visor, comprising:
  a curvilinear base having a first side portion, a second side portion, and a central portion disposed between the first and second side portions, the first and second side portions, and the central portion each having a top margin and a bottom margin respectively, where the bottom margin of the central portion extends past the bottom margin of the first and second side portions, the base including at least one recess, the at least one recess having a plurality of internal walls;
  a brim attached to, or formed with, the base, the brim being generally perpendicular to the base and positioned such that the brim is spaced between the top margin and the bottom margin of the central portion of the base; and
  at least one magnetic fastener received in the at least one recess to secure the base to the field mask, wherein at least one internal wall of the plurality of internal walls includes ribs to secure the at least one fastener to the at least one recess.

14. The visor of claim 13, wherein the at least one fastener and the at least one recess have corresponding trapezoidal shapes.

* * * * *